US007901931B2

(12) United States Patent
Cachon et al.

(10) Patent No.: US 7,901,931 B2
(45) Date of Patent: Mar. 8, 2011

(54) CELL FOR MEASURING BIOLOGICAL ACTIVITIES AND/OR PHYSIOLOGICAL PARAMETERS OF MICRO-ORGANISMS

(75) Inventors: Rémy Cachon, Dijon (FR); Yves Wache, Vougeot (FR); Duried Alwazeer, Homs (SY); Christophe Riondet, Saint-Appollinaire (FR); Patrick Guyondet, Chenove (FR); Charles Divies, Dijon (FR); Maryvonne Divies, legal representative, Dijon (FR)

(73) Assignee: Universite de Bourgogne, Dijon (FR)

( * ) Notice: Subject to any disclaimer, the term of this patent is extended or adjusted under 35 U.S.C. 154(b) by 1036 days.

(21) Appl. No.: 10/571,611

(22) PCT Filed: Sep. 13, 2004

(86) PCT No.: PCT/FR2004/002315
§ 371 (c)(1),
(2), (4) Date: Jan. 5, 2007

(87) PCT Pub. No.: WO2005/026714
PCT Pub. Date: Mar. 24, 2005

(65) Prior Publication Data
US 2008/0220511 A1    Sep. 11, 2008

(30) Foreign Application Priority Data
Sep. 11, 2003   (FR) ...................................... 03 10704

(51) Int. Cl.
*C12M 1/34*    (2006.01)
(52) U.S. Cl. ................. 435/287.1; 435/285.2; 435/302.1
(58) Field of Classification Search ............... 435/285.2, 435/287.1; 204/403.01, 403.06, 403.15
See application file for complete search history.

(56) References Cited

U.S. PATENT DOCUMENTS

| 3,471,393 A | 10/1969 | Ingruber |
| 4,288,544 A * | 9/1981 | Suzuki et al. ............... 205/777.5 |
| 5,254,461 A | 10/1993 | Rohrback et al. |
| 6,096,275 A | 8/2000 | Greenberg |

(Continued)

FOREIGN PATENT DOCUMENTS
EP    0 514 575    11/1996

(Continued)

OTHER PUBLICATIONS

Westerhoff et al."Magainins and the disruption of membrane-linked free-energy transduction." Proc. Natl. Acad. Sci. vol. 86 (Sep. 1989),pp. 6597-6601.*

(Continued)

*Primary Examiner* — William H Beisner
(74) *Attorney, Agent, or Firm* — Young & Thompson

(57) ABSTRACT

Device for the measurement of biological activities and/or physiological magnitudes, includes a measuring cell, equipped with a chamber suitable to receive micro-organisms to be analyzed, and one or more probes opening into the chamber. The probes are connected to measuring resources and resources for processing the electrical signals emitted by the probes. The measuring cell includes a vertical well, equipped in its lateral wall with holes uniformly distributed around the well in order to allow the probes to open into the well. The probes are sealingly attached to the well, and rest in the support resources, and suitable to receive a cup whose cross section is homothetic to the section of the well. The cup is equipped on its lateral wall with holes which are located opposite to the holes of the well when the cup is positioned in the well.

20 Claims, 2 Drawing Sheets

Figure 3:
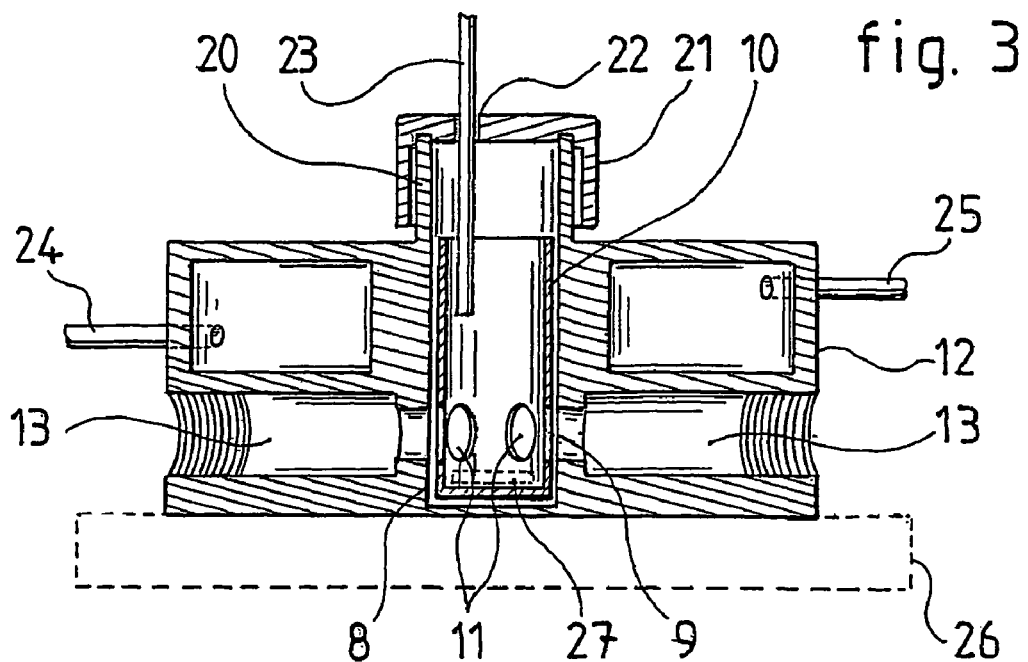

U.S. PATENT DOCUMENTS 6,375,829 B1 * 4/2002 Shevchenko et al. ...... 205/793.5
2004/0209351 A1 * 10/2004 Thielecke et al. ......... 435/287.1

FOREIGN PATENT DOCUMENTS

| FR | 1 356 645 | | 3/1964 |
|---|---|---|---|
| SU | 378761 A | * | 4/1977 |
| SU | 1 656 438 | | 6/1991 |

OTHER PUBLICATIONS

Database WPI 1991, Derwent Publications Ltd., London, GB; AN 1992-158551, XP002277572, Kholmukhamedov: "liquid medium testing device".

* cited by examiner

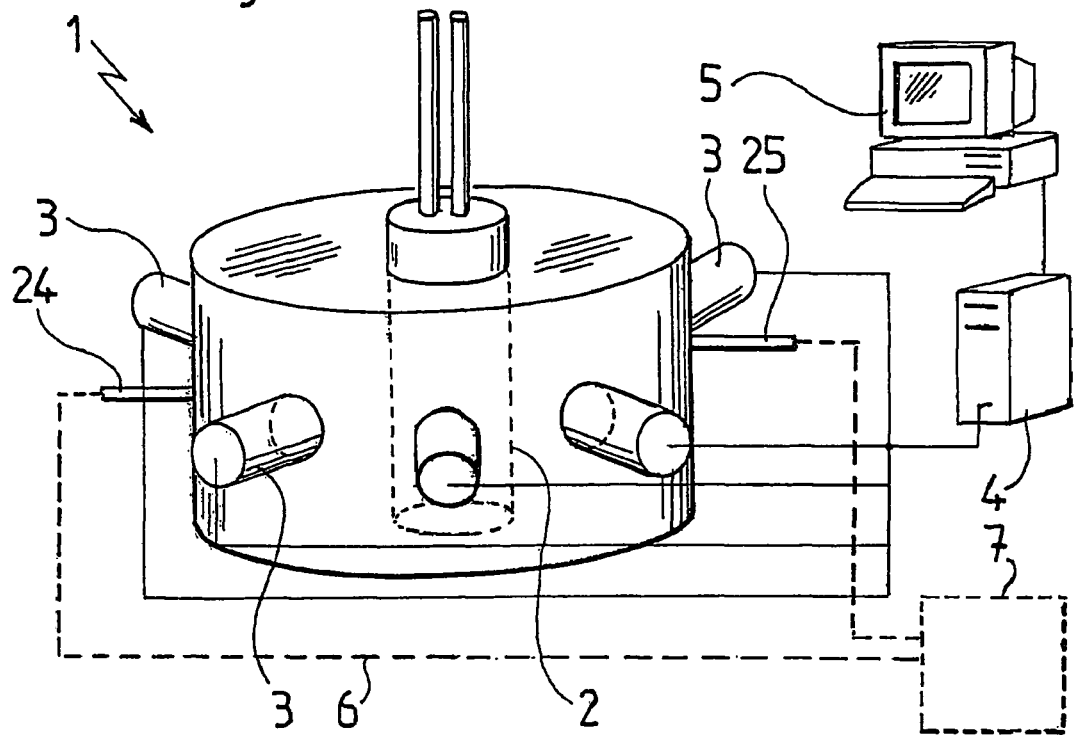
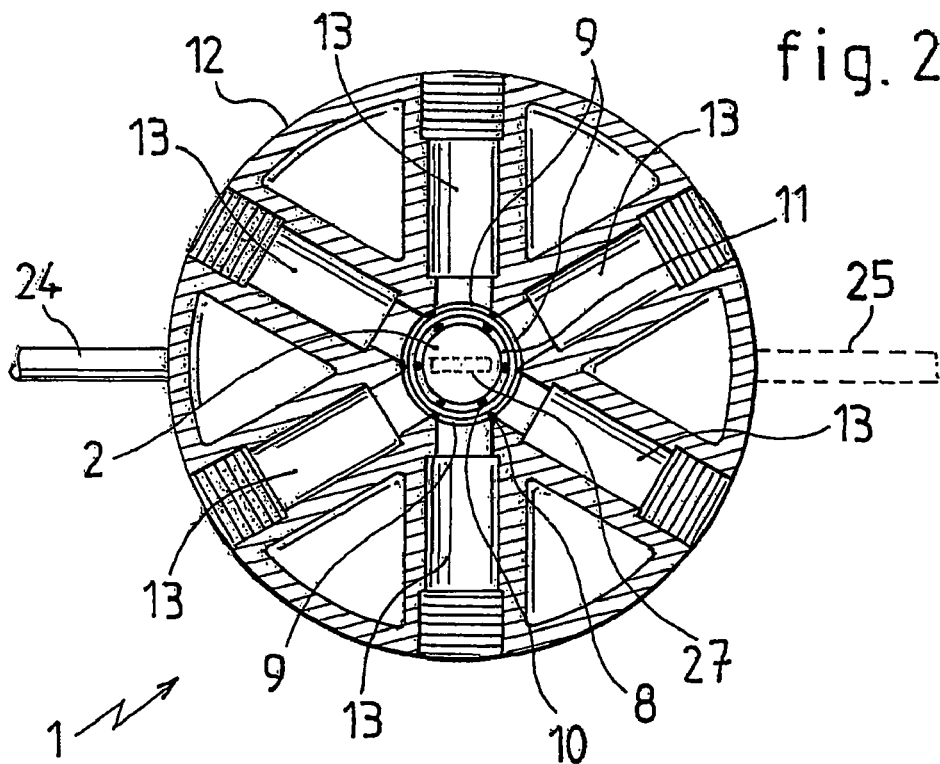

CELL FOR MEASURING BIOLOGICAL ACTIVITIES AND/OR PHYSIOLOGICAL PARAMETERS OF MICRO-ORGANISMS

This present invention concerns a device for the continuous measurement of biological activities and/or physiological magnitudes such as intracellular pH, the pH gradient ($\Delta$pH), the trans-membrane electrical gradient ($\Delta\psi$), the motive proton force, the enzymatic activity or similar, of cells such as bacteria or isolated enzymes for example, and/or for the culture of small volumes of micro-organisms.

We are already familiar with measurement of the intracellular pH ($pH_{in}$) of micro-organisms such as bacteria, given the role of the intracellular pH in the diverse vital physiological functions of the cells of these micro-organisms. In order to measure the $pH_{in}$ of micro-organisms, we are very familiar with methods involving pH indicators, such as the nuclear magnetic resonance spectroscopy (NMR) indicator $^{31}$P, and fluorescent pH probes. The measurement process with a pH indicator such as indicator $^{31}$P (NMR) is little used by researchers in the light of its complexity and of the excessive cost of the equipment necessary for the implementation of this process. In addition, the method using fluorescent probes cannot be used to measure the pHin of certain bacteria in particular. In fact, the value of the pHin of different bacteria can be between 5.6 and 9, so that since no probe is capable of covering this range of values, it is necessary to use a large number of probes, thus considerably increasing the cost of this method. Moreover, the fluorescent probes have low retention within the cell of certain bacteria, thereby rendering the method totally ineffective. It will also be seen that this type of process has the disadvantage that it prevents monitoring or control of the environment in which are the analysed cells are located.

In order to remedy these disadvantages, people have already put forward a method called "ion distribution", which is based on the assumption that the lipophylic neutral form of the probe is only permeable across the cytoplasmic membrane of the cells of the micro-organisms, and that the hydrophilic ionised form is impermeable. Thus, when the internal medium of the cell is alkaline in relation to the external medium, the neutral form of the probe penetrates the cellular membrane of the micro-organisms and dissolves in the cytoplasm as a function of its pKa and of the cytoplasmic pH until a state of equilibrium is attained. The flow from the external medium toward the interior across the membrane of the cell is detected and measured by an electrode that is sensitive to the lipophylic neutral form of the probe, which measures the concentration by measuring en electromotive force of the order of one millivolt, between an electrode made from platinum or gold, and a reference electrode immersed in the medium to be measured, with the said electromotive force manifesting itself by an electrical potential which is generated by the electrode and measured by the resources for processing the electrical signals.

Thus, people have already proposed cells such as the cell developed by the Dutch University of Groningen, in the laboratories of Professor Konings, which include a probe to measure the membrane potential of the micro-organisms commonly denoted $\Delta\psi$, a reference probe called the "calomel" electrode, and a probe for measuring the $\Delta$pH gradient, opening into a chamber suitable to receive the micro-organisms to be analysed, the said electrodes being connected to measuring resources and resources for processing the electrical signals emitted by the electrodes.

In addition, people have already proposed devices used for the measurement of biological activity and/or physiological magnitudes that include a measuring cell equipped with a chamber that is suitable to receive cells to be analysed, of the enzyme or micro-organism type, and with one or more probes which open into the chamber, where the probes are connected to measuring and processing resources, and where the measuring cell has a vertical well which is open at its upper part and closed at its lower part. The lateral wall of the well is equipped with holes so that the probes open into the well, the said probes being attached to the well in a sealed manner and resting in support resources distributed around the well. This is the case, for example, of American U.S. Pat. No. 6,096,275, or of the patent originating from the Soviet Union, numbered SU 16.56438.

Apart from these, French patent FR 2 779 525 describes an appliance consisting essentially of a support in which is placed a measuring card, a transfusion device, a thermostat, a measuring unit and a measurement management system. The measuring card includes a network of electrodes, one end of which opens into a chamber, and whose other end is placed outside this chamber. The micro-organisms are placed in the chamber, which is connected to the transfusion device, and the support includes a connector linking the electrodes of the card to the measurement management system by means of the measuring units allowing measurements to be taken continuously, and even remotely using a modem.

However, all these devices have the disadvantage of being difficult to clean so that bacteria from a previous experiment are liable to falsify the measurements of the next experiment.

In addition, the bioreactors have the disadvantage of requiring culturing of the micro-organisms to be studied in a large volume, which is frequently useless for the purposes of research. Moreover, it will be seen that the bioreactors have a particularly low area/volume ratio, so that the temperature is not homogeneous in the bioreactor in the event of thermal shock, which is liable to falsify the results of the experiment.

One of the objectives of the invention is therefore to remedy all these disadvantages by proposing a device for measuring biological activities and/or physiological magnitudes, of simple design and low cost, and allowing, in addition to the measurements, culturing of the micro-organisms in a small volume.

To this end and in accordance with the invention, a device is proposed for measuring physiological magnitudes such as intracellular pH, extracellular pH, motive proton force, enzymatic activity or similar, and that includes a cell, called the measuring cell, equipped with a chamber which is suitable to receive the micro-organisms to be analysed, and one or more probes opening into the chamber, the said probes being connected to measuring resources and resources for processing the electrical signals emitted by the electrodes, notable in that the measuring cell includes a vertical well of any cross section, open at its upper end and closed at its lower end, made from polyvinyl chloride (PVC), equipped on its lateral wall with holes distributed uniformly around the well to allow the probes to open into the well, the said probes being attached in a sealed manner to the well, and resting in support resources that are distributed uniformly around the well and attached to the said well, and suitable to receive a cup of cross section which is homothetic to the section of the well, and equipped on its lateral wall with holes which lie opposite to the holes of the well when the cup is positioned in the well, in order to allow the probes to open into the said cup in which the micro-organisms to be analysed are placed.

Figure 4:
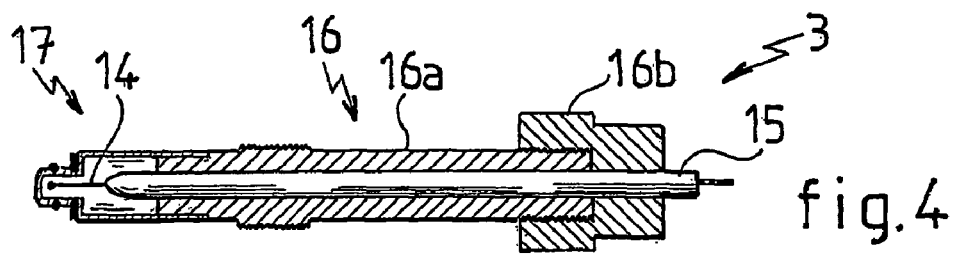
Figure 7:
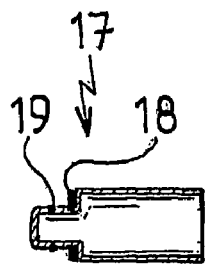
Figure 5:
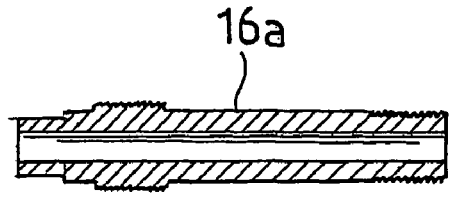
Figure 6:
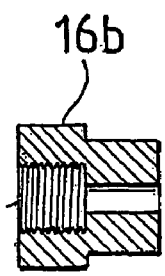
Figure 8:
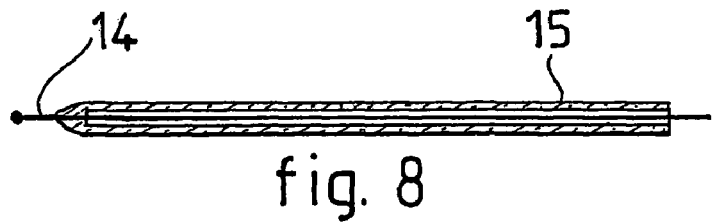

Other advantages and characteristics will emerge more clearly from the following description of the device for measuring the biological activities and/or physiological magnitudes of micro-organisms according to the invention, with reference to the appended figures in which:

FIG. 1 is a diagrammatic view in perspective of the device for measuring the biological activities and/or physiological magnitudes of micro-organisms according to the invention, FIG. 2 is a view in cross section seen on section line II-II' of FIG. 1 of the device according to the invention, FIG. 3 is a view in radial section seen on line III-III' of FIG. 2 of the device according to the invention, FIG. 4 is a view in longitudinal section of a probe of the device according to the invention, FIG. 5 is a longitudinal view of the duct of a probe of the device according to the invention, FIG. 6 is a view in longitudinal section of a second part of the duct of the probe of the device according to the invention, FIG. 7 is a view in longitudinal section of the membrane positioned at the distal end of the probe of the device according to the invention, FIG. 8 is a view in longitudinal section of an electrode constituting the probe of the device according to the invention.

In this non-limited example of implementation, we will describe a device for measuring biological activities and/or physiological magnitudes such as the intracellular pH, extracellular pH, pH gradient ($\Delta$pH), motive proton force, enzymatic activity or similar, of micro-organisms such as bacteria for example. However, the device can be adapted to other types of micro-organism, and to other types of measurement, while still remaining within the scope of the invention.

Referring to FIG. 1, the device according to the invention includes a cell, called the measuring cell 1, equipped with a chamber 2 suitable to receive the micro-organisms to be analysed, and one or more probes 3 opening into the chamber 2, the said probes 3 being connected to measuring resources 4 and resources 5 for processing the electrical signals emitted by the probes 3. The measuring resources 4 and the processing resources 5 can consist, for example, respectively of an electronic interface and a computer program installed on a computer of the PC type. In addition, the device advantageously includes resources for heating the micro-organisms placed in the chamber 2 of the measuring cell 1, consisting, for example, of a heating fluid circuit 6 at the periphery of the chamber 2 of the measuring cell 1 fed via thermal regulation resources 7, as will be detailed later.

Referring to FIGS. 2 and 3, the measuring cell 1 includes a vertical well 8 of circular cross section, open at its upper end and closed at its lower end, made from polyvinyl chloride (PVC), and equipped on its lateral wall, close to its bottom end, with holes 9 distributed uniformly around the well 8 to allow the probes 3 to open into the well 8, the said probes 3 being attached in a sealed manner to the well 8 and resting in support resources distributed uniformly around the well 8 and attached to the latter. It will be seen that in this particular example of implementation, all of the holes 9 made in the well 8 of the measuring cell 1 for the passage of the probes 3 are located at the same height in relation to the bottom of the said well 8. However, it is quite obvious that the holes 9 for the passage of the probes 3 can be made at different heights in relation to the bottom of the well 8 while still remaining within the scope of-the invention.

The measuring cell 1 includes, in addition, a cup 10 of homothetic circular cross section, with an outside diameter that is slightly less that the inside diameter of the well 8 of the measuring cell 1, suitable to be inserted in the said well 8, and equipped on its lateral wall with holes 11 which lie opposite to the holes 9 of the well 8 when the cup 10 is position in the latter, so as to allow the probes 3 to open into the said cup 10, in which the micro-organisms to be analysed are placed. This cup 10 is advantageously made from a metallic material which cannot be magnetised, such as stainless steel for example, to allow cleaning and sterilisation in particular.

It is quite obvious that the cup 10 can be made from any other non-magnetic materials that are suitable for sterilisation without damage, while still remaining within the scope of the invention.

Referring to FIGS. 2 and 3, the support resources of the probes consist of a section of cylindrical vertical hollow tube 12, closed at its upper and lower ends, with the well 8 lying coaxially so that the open top end of the well 8 coincides with the top end of the cylindrical tube 12. The cylindrical hollow tube 12 forming the support for the probes 3 includes horizontal passages 13, of circular cross section, distributed uniformly around the well 8 lying radially from the lateral wall of the tube forming the support 12 up to the lateral wall of the well 8, the said horizontal passages 13 being suitable to take the probes 3.

Referring to FIGS. 4 to 8, each probe 3 is composed of an electrode 14 resting in a closed glass tube 15 projecting at its distal and proximal ends. By the distal end of the electrode 14 is meant the end which opens into the cup 10, positioned within the well 8 of the measuring cell 1, while the proximal end refers to the end of the electrode 14 that projects from the cylindrical support tube 12 of the electrodes lying radially toward the exterior, and which is connected to the measuring resources 4 and to the resources 5 for processing the electrical signals emitted by the said electrode 14. The glass tube 15 in which the electrode 14 lies is filled with a solution and it is enveloped by a duct 16 that consists of two parts, namely a main generally cylindrical part 16a whose outside diameter is just less than the inside diameter of the passages 13, and a second generally cylindrical part 16b designed to fit into the proximal end of part 16a of the duct 16 and whose outside diameter is greater than the inside diameter of the passages 13, the said parts 16a and 16b of the duct 16 being made from an elastically deformable material in order to allow the blocking of the probe 3 in the passage 13 when it is inserted into the said passage 13. In addition, the distal end of the electrode 14 is capped by a hollow and rigid membrane 17, suitable to fit into the distal end of the first part 16a of the duct 16 enveloping the glass tube 15 in which the electrode 14 lies.

It goes without saying that the membrane 17 can be screwed at the distal end of the first part 16a of the duct 16, which includes a screw thread for this purpose, while still remaining within the scope of the invention.

This membrane 17 of generally cylindrical shape includes at its free end a cutting-back of its section, fitted with o-rings 18 and 19 designed to rest respectively against the external wall of the well 8 and the edge of the holes 11 made in the cup 10 inserted into the well 8 of the measuring cell 1 in order to provide a seal for the cup 10.

In a particularly advantageous manner, the device includes a probe 3 which has an electrode rendered selective to salicylate, in order to measure the internal pH ($pH_{in}$) of the micro-organisms, which is used to deduce the $\Delta$pH gradient of the micro-organisms which is equal to the difference between the external pH and the internal pH, namely:

$$\Delta pH = pH_{in} - pH_{ext}$$

The probe for measuring $pH_{in}$ is composed of an electrode made from platinum chloride, resting in a closed glass tube projecting at its distal and proximal ends, the said glass tube 15 being filled with a solution of salicylate at a concentration of 2 mM, and the distal end of the electrode 14 being capped by a polyvinyl chloride (PVC) membrane 17 treated with tetraheptylammonium iodide. The external pH is measured by means of a probe 3 which is conventionally composed of an electrode called the combined electrode, meaning an electrode that includes a second reference electrode, made from platinum and resting in a glass tube 15 filled with a solution of silver, silver chloride and saturated Kcl, the distal end of the electrode 14 being capped by a glass membrane 17 allowing the H30+ ions to pass.

In addition, the device includes a probe 3 which has an electrode that is rendered selective to tetraphenylphosphonium (TPP+) to measure the membrane potential, commonly denoted $\Delta\psi$. This probe for measuring the membrane potential, $\Delta\psi$, is composed of an electrode 14 made from platinum chloride resting in a closed glass tube 15 projecting at its distal and proximal ends, the said tube 15 being filled with a solution of tetraphenylphosphonium (TPP+), the distal end of the electrode 14 being capped by a PVC membrane 17 treated with tetraphenylboride. In order to allow measurement of the membrane potential, $\Delta\psi$, and of $pH_{in}$, the device includes a reference probe 3, called a calomel electrode, composed of an electrode 14 made from mercury covered with calomel ($Hg_2Cl_2$) resting in a closed glass tube 15 projecting at its distal and proximal ends, the said glass tube 15 being filled with a solution of potassium chloride saturated with calomel. In addition, the device can advantageously include a probe 3 for measuring the redox potential $E_h$, or indeed a probe 3 that includes an electrode to measure the dissolved oxygen.

In a particularly advantageous manner, referring to FIGS. 1 and 3, the top end of the well 8 of the measuring cell 1 includes a neck 20 that is suitable to be capped by a cover 21, made from rubber or PVC for example, closing off the well 8 in a sealed manner. Moreover, the cover 21 advantageously includes holes 22 in which closable conduits are placed in order to allow the introduction and/or removal of materials respectively to and from the cup 10. These conduits 23 thus allow the escape of gases produced by the micro-organisms, or indeed the introduction or the sampling of micro-organisms in the cup 10, or again the introduction of a gas into the cup 10 in order to allow the study of micro-organisms in different atmospheric compositions and/or different pressure conditions.

It goes without saying that the cover can consist of a screwed cap equipped at its end with a sealing element that is suitable to fit against on the top edge of the neck 20, where the latter has a screw thread.

In addition, referring to FIGS. 1 to 3, the device advantageously includes a conduit 24 for the admission of a heat-bearing fluid such as hot or cold water, opening into the space formed between the lateral wall of the cylindrical support tube 12 and the lateral wall of the well 8 of the measuring cell 1, and a second outlet conduit 25 for the water, diametrically opposite to the admission conduit 24, the said admission 24 and escape 25 conduits being connected, via a circuit 6, to thermal regulation resources 7 that include, for example, a thermistor and temperature control/monitoring resources connected to a thermostat. In order to allow monitoring of the temperature of the micro-organisms placed in the cup 10 of the measuring cell 1, the device will advantageously include a thermostatic probe opening into the said cup 10.

In order to allow the use of the measuring cell 1 as a bioreactor, the device includes resources for stirring the micro-organisms, composed of a base 26, shown by dotted lines in FIG. 3, on which the well 8 rests, and which includes a rotating magnet or alternately excited coils as described in French patent FR 2 539 053 for example, suitable for driving a stirring rod 27 placed at the bottom of the cup 10 of the device.

According to a particularly advantageous implementation variant of the measuring cell according to the invention, the lateral wall of the vertical well 8 is made from a heat-conducting material such as stainless steel, glass or similar, in order to favour thermal transfer of the heat-bearing fluid which is in contact with the lateral outer wall of the vertical well 8 toward the micro-organisms contained in the said well 8.

Finally, it goes without saying that the probes can consist of any appropriate probe, and that the examples that have just been given are merely particular illustrations which under no circumstances limit the areas of application of the invention.

The invention claimed is:

1. A device for measuring biological activities and/or physiological magnitudes comprising:
    a measuring cell (1) equipped with a chamber (2) that is suitable to receive cells to be analysed; and one or more probes (3) opening into the chamber (2), the probes (3) being connected to measuring resources (4) and resources for processing (5) electrical signals emitted by the probes (3);
    wherein the measuring cell (1) comprises a vertical well (8) of any cross section;
    wherein the vertical well (8) is open at its upper end and closed at its lower end, said lower end being made from polyvinyl chloride (PVC), and equipped on its lateral wall with holes (9) distributed uniformly around the well (8) so as to allow the probes (3) to open into the well (8),
    wherein said probes (3) are attached to the well (8) in a sealed manner, and are resting in support resources (12) distributed uniformly around the well (8), attached to the latter, and
    a removable cup (10) of cross section that is homothetic to the section of the well (8) and equipped on its lateral wall with holes (11) which lie opposite to the holes (9) of the well (8) when the cup (10) is positioned in the well (8) so as to allow the probes (3) to open into said cup (10) in which the micro-organisms to be analysed are placed,
    said cup being made from a metallic material that can be sterilised without damage.

2. A device according to claim 1, wherein the support resources (12) of the probes (3) are hollow and lie around the well (8) of the measuring cell (1) in order to allow the circulation of a heat-bearing fluid around said well (8), the heat-bearing fluid being supplied via a heat-regulation unit (7).

3. A device according to claim 2 wherein the support resources (12) of the probes (3) consist of a section of hollow vertical tube (12), closed at its upper and lower ends, with the well (8) lying coaxially so that the top end of the well (8) coincides with the top end of the tube (12), and fitted with horizontal passages, distributed uniformly around the well (8), extending from the lateral wall of the tube (12) up to the lateral wall of the well (8) and suitable to take the probes (3).

4. A device according to either of claim 2, wherein the lateral wall of the vertical well (8) is made from a heat-conducting material in order to favour thermal transfer from the heat-bearing fluid which is in contact with the lateral outer wall of the vertical well (8) toward the micro-organisms contained in the well (8).

5. A device according to claim 4, wherein the heat-conducting material is stainless steel.

6. A device according to claim 4, wherein the heat-conducting material is glass.

7. A device according to any of claim 3, wherein the well (8), the cup (10), and the tube (12), are of circular cross section.

8. A device according to claim 1, wherein each probe (3) is fitted with a duct (16) with a section that is just smaller than the section of the passages (13), made from a material which is conventionally deformable in order to allow blocking of the probe (3) in the passage (13) when the probe (3) fitted with its duct (16) is inserted into the passage (13), with the distal and proximal ends of the probe (3) projecting from the said duct (16).

9. A device according to claim 8, wherein each probe (3) is composed of an electrode (14) resting in a closed glass tube (15) projecting at its distal and proximal ends, the said glass tube (15) being filled with a solution and the distal end of the electrode (14) being capped by a membrane (17).

10. A device according to claim 1, wherein the probe (3) comprises an electrode (14) which is rendered selective to salicylate in order to measure the $\Delta$pH gradient of the microorganisms.

11. A device according to claim 10, wherein the probe for measuring the $\Delta$pH gradient is composed of an electrode (14) made from platinum chloride resting in a closed glass tube (15) projecting at its distal and proximal ends, with the said glass tube (15) being filled with a solution of salicylate, and the distal end of the electrode (14) being capped by a polyvinyl chloride (PVC) membrane treated with the tetraheptylammonium iodide.

12. A device according to claim 11, wherein the solution of salicylate has a concentration of 2 mM.

13. A device according to claim 1, wherein the probe (3) comprises an electrode which is rendered selective to tetraphenylphosphonium (TPP+) in order to measure the membrane potential, $\Delta\psi$.

14. A device according to claim 13, wherein the probe (3) for measuring the membrane potential, $\Delta\psi$, is composed of an electrode (14) made from platinum chloride, resting in a closed glass tube (15) and projecting at its distal and proximal ends, the said glass tube (15) being filled with a solution of tetraphenylphosphnium (TPP+) and the distal end of the electrode (14) being capped by a PVC membrane (17) treated with tetraphenylboride.

15. A device according to claim 1, further comprising a reference probe (3) made from mercury covered with calomel ($Hg_2Cl_2$) resting in a closed glass tube (15), projecting at its distal and proximal ends, the glass tube (15) being filled with a solution of potassium chloride saturated with calomel.

16. A device according to claim 1 further comprising a probe (3) for measuring pH.

17. A device according to claim 1, further comprising a probe (3) for measuring the redox potential, Eh.

18. A device according to claim 1, wherein the top end of the well (8) includes a neck (20) that is suitable to be capped by a cover (21) closing off the well in a sealed manner (8).

19. A device according to claim 18, wherein the cover (21) comprises at least one orifice (22) which can be capped, to allow the introduction and/or the removal of material respectively into and out of the well (8).

20. A device according to claim 1, further comprising stirring resources composed of a base (26) on which the well (8) rests, and a rotating magnet or alternately excited coils suitable for driving a stirring rod (27), placed at the bottom of the cup (10) of the device.

* * * * *